United States Patent [19]
Ito et al.

[11] Patent Number: 5,886,009
[45] Date of Patent: Mar. 23, 1999

[54] QUINUCLIDINE DERIVATIVE AS A SUBSTANCE P ANTAGONIST

[75] Inventors: Fumitaka Ito, Chita-Taketoyo; Hiroshi Kondo, Handa; Masami Nakane, Showakyu; Kaoru Shimada, Okazaki, all of Japan

[73] Assignee: Pfizer Inc., New York, N.Y.

[21] Appl. No.: 500,958

[22] PCT Filed: Jul. 19, 1993

[86] PCT No.: PCT/US93/06624

§ 371 Date: Jun. 19, 1995

§ 102(e) Date: Jun. 19, 1995

[87] PCT Pub. No.: WO94/11368

PCT Pub. Date: May 26, 1994

Related U.S. Application Data

[63] Continuation of Ser. No. 975,244, Nov. 12, 1992, abandoned.

[51] Int. Cl.$^6$ .................. A61K 31/435; C07D 453/02
[52] U.S. Cl. ............................. 514/305; 546/133
[58] Field of Search ............... 546/133; 514/305

[56] References Cited

U.S. PATENT DOCUMENTS

| | | | |
|---|---|---|---|
| 5,360,820 | 11/1994 | Hagan | 514/559 |
| 5,451,586 | 9/1995 | Lowe | 514/305 |
| 5,519,033 | 5/1996 | Rosen | 514/305 |

FOREIGN PATENT DOCUMENTS

WO 90/05729  5/1990  WIPO.
WO 92/21677  12/1992  WIPO.

OTHER PUBLICATIONS

Parnet, P. et al., Abstract from Gastro–Enterologica Belgica., Supplement, 1993, p. 64.
Blaser, M.J., Gastroenterology, 1992, 102, pp. 720–727.
Beding–Barnekow, B. et al., Br. J. Pharmcol. 1988,95(1), pp. 259–267.
Holmdahl, G. et al., Science, 1981, 214(4524), pp. 1029–1031.
Krupin, T. et al., Exp. Eye, Res., 1982, 34(3), pp. 319–324.
Tiseo, P.J. et al., CIBA Foundation Symposium, 1990, 151, pp. 91–104.
Merck Manual, edited by Berkow et al., 16th ed., 1992, Merck Research Labs, pp. 306, 815–816, 1308–1312, 1582–1583, 1603–1614, and 1635.

*Primary Examiner*—Alan L. Rotman
*Assistant Examiner*—Charanjit S. Aulakh
*Attorney, Agent, or Firm*—Peter C. Richardson; Paul H. Ginsburg; Karen DeBenedictis

[57] ABSTRACT

This invention relates to the quinuclidine derivative (2S, 3S)-N-(5-n-propyl-2-methoxyphenyl)methyl-2-diphenylmethyl-1-azabicyclo[2.2.2]octan-3-amine and its pharmaceutically acceptable salts. These compounds are substance P antagonists and are useful in the treatment of gastrointestinal disorders, inflammatory disorders, central nervous system disorders and pain.

3 Claims, No Drawings

QUINUCLIDINE DERIVATIVE AS A SUBSTANCE P ANTAGONIST

This application is a 371 of PCT/US93/06624, Jun. 19, 1993, which is now published as WO 94/11368 on May 28, 1994 and which is a continuation of U.S. Ser. No. 07/975,244, which was filed on Nov. 12, 1992 now abandoned.

BACKGROUND OF THE INVENTION

The present invention relates to the novel quinuclidine derivatives (2S,3S)-N-(5-n-propyl-2-methoxyphenyl)methyl-2-diphenylmethyl-1-azabicyclo[2.2.2]octan-3-amine, pharmaceutical compositions comprising such compound and the use of such compound in the treatment and prevention of inflammatory and central nervous system disorders, as well as several other disorders. The pharmaceutically active compound of this invention is a substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

The quinuclidine derivative of this invention is referred to generically in U.S. Pat. No. 5,162,339, which issued to John A. Lowe III on Nov. 11, 1992.

Quinuclidine, piperidine, and azanorbornane derivatives and related compounds that exhibit activity as substance P receptor antagonists are referred to in U.S. patent application Ser. No. 724,268, filed Jul. 1, 1991, PCT Patent Application PCT/US 91/02853, filed Apr. 25, 1991, PCT Patent Application PCT/US 91/03369, filed May 14, 1991, PCT Patent Application PCT/US 91/05776, filed Aug. 20, 1991, PCT Patent Application PCT/US 92/00113, filed Jan. 17, 1992, PCT Patent Application PCT/US 92/03571, filed May 5, 1992, PCT Patent Application PCT/US 92/03317, filed Apr. 28, 1992, PCT Patent Application PCT/US 92/04697, filed Jun. 11, 1992, U.S. patent application Ser. No. 766,488, filed Sep. 26, 1991, U.S. patent application Ser. No. 790,934, filed Nov. 12, 1991, PCT Patent Application PCT/US 92/04002, filed May 19, 1992, Japanese Patent Application No. 065337/92, filed Mar. 23, 1992, and U.S. patent application Ser. No. 932,392, filed Aug. 19, 1992.

SUMMARY OF THE INVENTION

The present invention relates to the quinuclidine derivative (2S,3S)-N-(5-n-propyl-2-methoxyphenyl)methyl-2-diphenylmethyl-1-azabicyclo[2.2.2]octan-3-amine and its pharmaceutically acceptable salts.

(2S,3S)-N-(5-n-Propyl-2-methoxyphenyl)methyl-2-diphenylmethyl-1-azabicyclo[2.2.2]octan-3-amine has the following chemical structure

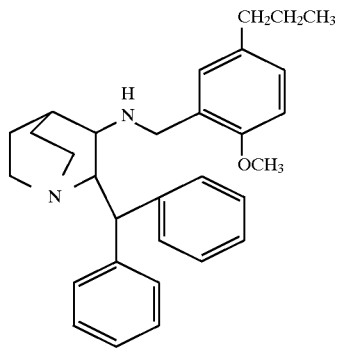

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of (2S,3S)-N-(5-n-propyl-2-methoxyphenyl)methyl-2-diphenylmethyl-1-azabicyclo[2.2.2]octan-3-amine, or a pharmaceutically acceptable salt thereof.

The present invention also relates to a pharmaceutical composition for treating or preventing a disorder in a mammal, including a human, resulting from an excess of substance P, comprising a substance P antagonizing amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of (2S,3S)-N-(5-n-propyl-2-methoxyphenyl)methyl-2-diphenylmethyl-1-azabicyclo[2.2.2]octan-3-amine, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of (2S,3S)-N-(5-n-propyl-2-methoxyphenyl)methyl-2-diphenylmethyl-1-azabicyclo[2.2.2]octan-3-amine, or a pharmaceutically acceptable salt thereof, effective in treating or preventing such disorder.

DETAILED DESCRIPTION OF THE INVENTION (2S,3S)-N-(5-n-Propyl-2-methoxyphenyl)methyl-2-diphenylmethyl-1-azabicyclo[2.2.2]octan-3-amine (hereinafter also referred to as "the active compound of this invention") may be prepared by subjecting a compound of the formula

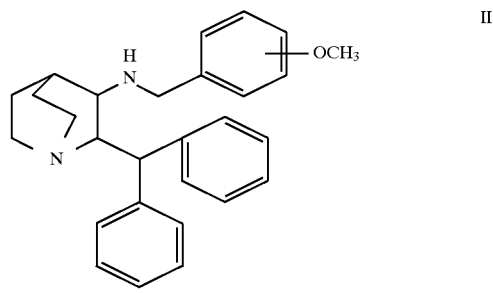

having the same absolute stereochemistry as the active compound of this invention, to hydrolytic removal of the methoxybenzyl group to produce the corresponding compound of the formula

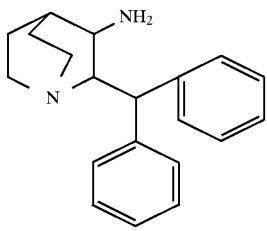

having the same stereochemistry, and then reacting the compound of formula III so formed with an aldehyde of the formula

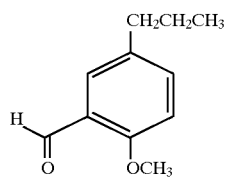

in the presence of a reducing agent.

Hydrolytic removal of the methoxybenzyl group is generally carried out using a strong mineral acid such as hydrochloric, hydrobromic or hydroiodic acid, at a temperature from about room temperature to about the reflux temperature of the acid. Preferably, the reaction is conducted in hydrobromic acid at the reflux temperature. This reaction is usually carried out for a period of about 2 hours.

Alternatively, the hydrolytic removal of the methoxybenzyl group in the above procedure may be replaced by hydrogenolytic removal of such group. Hydrogenolytic removal is generally accomplished using hydrogen in the presence of a metal containing catalyst such as platinum or palladium. This reaction is usually conducted in a reaction inert solvent such as acetic acid or a lower alcohol, at a temperature from about 0° C. to about 50° C. The methoxybenzyl group may also be removed, alternatively, by treating the compound of formula II with a dissolving metal such as lithium or sodium in ammonia at a temperature from about −30° C. to about 78° C., or with a formate salt in the presence of palladium or with cyclohexane in the presence of palladium.

Preferably, the methoxybenzyl group is removed by treating the compound of formula II with hydrogen in the presence of palladium hydroxide on carbon in methanol containing hydrochloric acid at a temperature of about 25° C.

The resulting compound of formula III may be converted into the active compound of this invention by reaction with the aldehyde of formula IV in the presence of a reducing agent. The reaction is typically carried out using a reducing agent such as sodium cyanoborohydride, sodium triacetoxyborohydride, sodium borohydride, hydrogen and a metal catalyst, zinc and hydrochloric acid, borane dimethylsulfide or formic acid at a temperature from about −60° C. to about 50° C. Suitable reaction inert solvents for this reaction include lower alcohols (e.g., methanol, ethanol and isopropanol), acetic acid, methylene chloride and tetrahydrofuran (THF). Preferably, the solvent is methylene chloride, the temperature is about 25° C., and the reducing agent is sodium triacetoxyborohydride.

Alternatively, the reaction of the compound of the formula III with the compound of the formula IV may be carried out in the presence of a drying agent or using an apparatus designed to remove azeotropically the water generated, to produce an imine of the formula

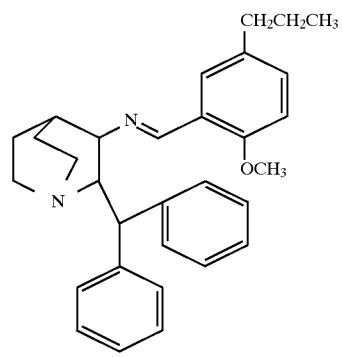

which is then reacted with a reducing agent as described above, preferably with sodium triacetoxyborohydride at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane, titanium isopropoxide/dichloromethane and molecular sieves/THF. Titanium tetrachloride/dichloromethane is preferred.

The active compound of this invention may also be prepared from a compound of the formula III having the same stereochemistry by reacting the compound of formula III with a compound of the formula

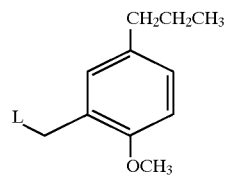

wherein L is a suitable leaving group (e.g., chloro, bromo, iodo or mesylate). This reaction is generally carried out in a reaction inert solvent such as dichloromethane or THF, preferably dichloromethane, at a temperature from about 0° C. to about 60° C., preferably at about 25° C.

The active compound of this invention may also be prepared from a compound of the formula III having the same stereochemistry by reacting the compound of formula III with a compound of the formula

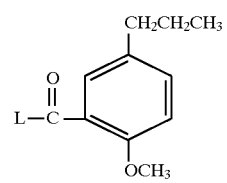

wherein L is defined as above or is imidazole, and then reducing the resulting amide. This reaction is typically carried out in an inert solvent such as THF or dichloromethane at a temperature from about −20° C. to about 60° C., preferably in dichloromethane at about 0° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

The active compound of this invention and its pharmaceutically acceptable salts are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

(2S,3S)-N-(5-n-Propyl-2-methoxyphenyl)methyl-2-diphenylmethyl-1-azabicyclo[2.2.2]octan-3-amine is basic in nature and therefore capable of forming a wide variety of different salts with various inorganic and organic acids. Although such salts must be pharmaceutically acceptable for administration to animals, it is often desirable in practice to initially isolate the active compound of this invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active compound of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compound of this invention and its pharmaceutically acceptable salts exhibit substance P receptor binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The active compound of this invention and its pharmaceutically acceptable salts can be administered via either the oral, parenteral or topical routes. In general, these compounds are most desirably administered in dosages ranging from about 0.5 mg to about 500 mg per day, although variations will necessarily occur depending upon the weight and condition of the subject being treated and the particular route of administration chosen. Variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compound of this invention and its pharmaceutically acceptable salts may be administered alone or in combination with pharmaceutically acceptable carriers or diluents by either of the three routes previously indicated, and such administration may be carried out in single or multiple doses. More particularly, such compounds can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compound of this invention or a pharmaceutically acceptable salt thereof is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the active compound of this invention, or a pharmaceutically acceptable salt thereof, in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compound of this invention and its pharmaceutically acceptable salts topically when treating inflammatory conditions of the skin and this may preferably be done by way of creams, jellies, gels, pastes, ointments and the like, in accordance with standard pharmaceutical practice.

The activity of the active compound of this invention and its pharmaceutically acceptable salts as substance P receptor antagonists may be determined by its ability to inhibit the binding of substance P at its receptor sites in bovine caudate tissue, employing radioactive ligands to visualize the tachykinin receptors by means of autoradiography. The substance P antagonizing activity of such compounds may be evaluated by using the standard assay procedure described by M. A. Cascieri et al., as reported in the *Journal of Biological Chemistry*, Vol. 258, p. 5158 (1983). This method essentially involves determining the concentration of the active compound of this invention, or a pharmaceutically acceptable salt thereof, required to reduce by 50% the amount of radiolabelled substance P ligands at their receptor sites in said isolated cow tissues, thereby affording characteristic $IC_{50}$ values for the compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the active compound of this invention and its pharmaceutically acceptable salts as neuroleptic agents for the control of various psychotic disorders may be determined primarily by a study of its ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following example. It will be understood, however, that the invention is not limited to the specific details of this example.

EXAMPLE (2S,3S)-N-(2-Methoxy-5-n-propylphenyl)methyl-2-diphenymethyl-1-azabicyclo[2.2.2]octan-3-amine methanesulfanate To a solution of a 2-methoxy-5-n-propylbenzaldehyde (370 mg, 2.06 mmol) (prepared by Duff's formylation of 4-n-propylanisole, as desribed in *Synth. Common.*, 15, 61 (1985)) and (2S,3S)-diphenylmethyl-1-azabicyclo-[2,2,2] octan-3-amine (1.71 mmol) in methylene chloride (20 ml) was added in portions sodium triacetoxyborohydride (510 mg. 2.39 mmol). The mixture was stirred until the amine disappeared. Thesolution was carefully neutralized with an ice cooled 2N sodium hydroxide solution. The organic layer was washed with water, dried over magnesium sulfate, and concentrated to give the product (840 mg), which was chromatographed on a silica gel column. $^1$H NMR (270 MHz, $CDCl_3$, ppm): δ 10.45 (s, 1H), 7.64 (d, J=2.6 Hz, 1H), 7.37 (dd, J=8.4, 2.6 Hz, 1H), 6.91 (d, J=8.4 Hz, 1H), 3.91 (s, 3H), 2.56 (t, J=7.3 Hz, 2H), 1.62 (m, 2H), 0.92 (t, J=7.3 Hz, 3H).

Methanesulfonic acid (96 μl) was added to the product (650 mg). The precipitate was recrystallized from acetone to give the analytical pure product (240 mg).

M.P.: 237°–241° C. (acetone).

Analysis calc'd for $C_{31}H_{38}N_2O \cdot CH_3SO_3H \cdot 1/3H_2O$: C, 69.04%; H, 7.72%; N, 5.03%. Found C, 68.96%; H, 7.88%; N, 4.99%.

$^1$H NMR (270 MHz, $CDCl_3$, ppm): δ 7.36–7.04 (m, 10H), 6.94 (dd, J=8.4, 2.5 Hz, 1H), 6.62 (d, J=8.4 Hz, 1H), 6.46 (d, J=2.5 Hz, 1H), 4.50 (d, J=12.0 Hz, 1H), 3.68 (dd, J=12.0, 8.0 Hz, 1H), 3.58 (d, J=14.0 Hz, 1H), 3.54 (s, 3H), 3.22 (d, J=14.0 Hz, 1H), 3.27–3.15 (m, 1H), 2.92 (dd, J=8.0, 4.0 Hz, 1H), 2.76 (m, 2H), 2.60 (m, 1H), 2.44 (t, J=7.4 Hz, 2H), 2.07 (m, 1H), 1.97–1.89 (m, 1H), 1.70–1.45 (m, 4H), 1.31–1.20 (m, 1H), 0.94 (t, J=7.4 Hz, 3H).

$^{13}$C NMR (67.5 MHz, $CDCl_3$, ppm): δ 155.5, 145.6, 143.3, 134.1, 129.4, 128.9, 128.3, 127.6, 127.5, 127.4, 126.3, 125.8, 109.8, 61.9, 55.3, 54.6, 49.4, 49.2, 46.5, 41.9, 37.1, 25.5, 24.9, 24.7, 19.9, 13.9.

IR (KBr): 3,410 (br.), 1,502 (s), 1,455 (m), 1,300–1,100 (br, m), 753 (s), 710(s).

What is claimed is:

1. (2S,3S)-N-(5-n-propyl-2-methoxyphenyl)methyl-2-diphenylmethyl-1-azabicyclo[2.2.2]octan-3-amine and its pharmaceutically acceptable salts.

2. A pharmaceutical composition comprising an amount of a therapeutically effective amount of a compound according to claim 1 and a pharmaceutically acceptable carrier.

3. A pharmaceutical composition according to claim 2, wherein the concentration of the compound according to claim 1 is from about 5.0% to about 70.0% by weight.

* * * * *